Figure 1:
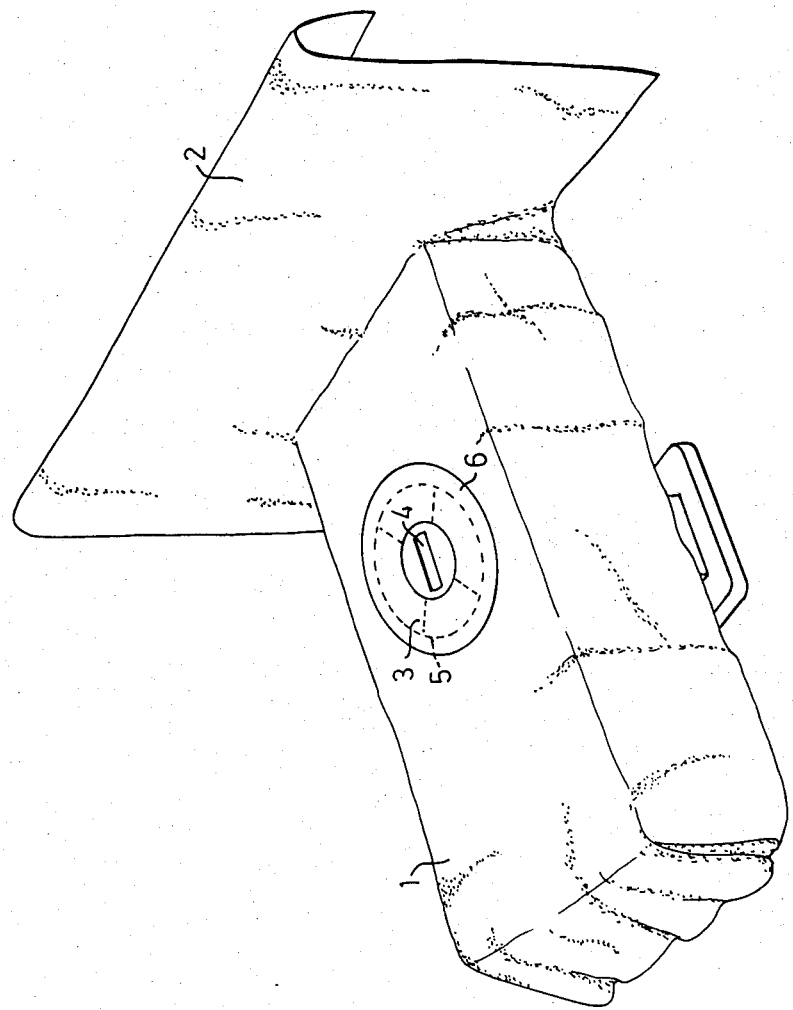

United States Patent [19]

Hanssen

[11] Patent Number: 4,607,631

[45] Date of Patent: Aug. 26, 1986

[54] ARRANGEMENT IN SURGICAL SHEETS

[75] Inventor: Carl-Otto Hanssen, Kullavik, Sweden

[73] Assignee: Molnlycke AB, Gothenburg, Sweden

[21] Appl. No.: 663,041

[22] Filed: Oct. 16, 1984

[30] Foreign Application Priority Data

Oct. 28, 1983 [SE] Sweden .............................. 8305944

[51] Int. Cl.⁴ ............................................ A61F 13/00
[52] U.S. Cl. ................................................ 128/132 D
[58] Field of Search ........................ 128/132 D, 132 R

[56] References Cited

U.S. PATENT DOCUMENTS

| 3,921,627 | 11/1975 | Wilson et al. | 128/132 D |
| 4,024,862 | 5/1977 | Collins | 128/132 D |
| 4,336,797 | 6/1982 | Latucca et al. | 128/132 D |

FOREIGN PATENT DOCUMENTS 2003035  3/1979  United Kingdom .......... 128/132 D

Primary Examiner—Mickey Yu
Attorney, Agent, or Firm—Young & Thompson

[57] ABSTRACT

The invention relates to an arrangement in surgical sheets of the kind which are provided with a hole which is intended to be placed over the area of a patient where an operation is to be performed. The arrangement according to the invention is characterized in that a disk having arranged therein an elongated opening is intended to cover the hole in the sheet and can be adjusted to different positions of rotation with the longitudinal axis of the opening extending in the direction of an intended surgical incision.

6 Claims, 3 Drawing Figures

ARRANGEMENT IN SURGICAL SHEETS

The present invention relates to an arrangement in surgical sheets which are provided with at least one through-passing relatively large hole which, when using the sheet, is intended to be positioned over the area of a patient at which an operation is to be performed.

At present there are to be found two separate surgical sterilized sheet-systems with which a patient can be covered in a sterile fashion in conjunction with surgical operations. One such system is a multi-sheet system, in which, for example, four separate sheets are placed in mutually overlapping relationship in a manner to cover the patient while leaving exposed the body area at which the operation is to be performed. Multi-sheet systems also include so-called wear-sheets, which may comprise, for example, a sheet having a U-shaped edge slit therein, this sheet being placed with the slit located in the body region where an incision is to be made, and one or more additional sheets for covering the remainder of the patient. Although with a multi-sheet system it is possible to arrange the various sheets in a manner suitable to perform the majority of operation incisions, the actual task of laying and arranging the sheets is both complicated and time consuming. As will be understood, the fact that the sheets of such a system must be manipulated a large number of time in order to cover the patient satisfactorily, means that the risk of contamination is greater than when the sterilized sheets can be lain with fewer manipulations.

The other of the abovementioned two systems comprises the use of so-called hole-sheets. One serious disadvantage with this system is that a large number of sheets with mutually different hole configuration must be available, in order to enable different operations to be performed.

In accordance with the invention there is now provided an arrangement with which the aforementioned disadvantages associated with known sheet-laying or sheet-covering systems are fully eliminated.

Taking its point of departure from a surgical sheet of the kind described in the introduction, an arrangement according to the invention is mainly characterized by a preferably circular disk which has therein an elongated relatively small opening and which comprises at least two layers, of which one is formed from a liquid-impermeable material, which disk covers the hole in the surgical sheet, can be adjusted to selected positions of rotation with the longitudinal axis of the elongated opening extending along the line of the intended incision, and is provided with fastener means, for example self-adhesive binder, for securing the disk in its adjusted position in relation to the sheet and/or the body of the patient.

In accordance with a preferred embodiment of this arrangement, the disk comprises two liquid-impermeable layers, which are turned towards each other and are mutually joined along a substantially peripheral line defining the disk-opening and along a plurality of radially extending lines, and that the layer remote from the patient when the disk is in use has a central circular area free from the overlying said layer, whose diameter exceeds the length of the disk-opening, thereby to form firstly a worksurface located around the disk-opening, and secondly a plurality of pockets which are open towards the worksurface and which are defined laterally by adjacently lying radial connecting lines and at the bottom by the peripherally extending connecting line, and which serve to take-up liquid and/or surgical auxiliary devices.

The disk is preferably permanently fixed in the through-passing hole in the surgical sheet, wherewith peripheral parts of the layers of material in the disk overlap mutually opposite sheet parts located nearest the hole and the material layers are joined at least along a circumferential line radially within the peripheral portions.

Figure 2:
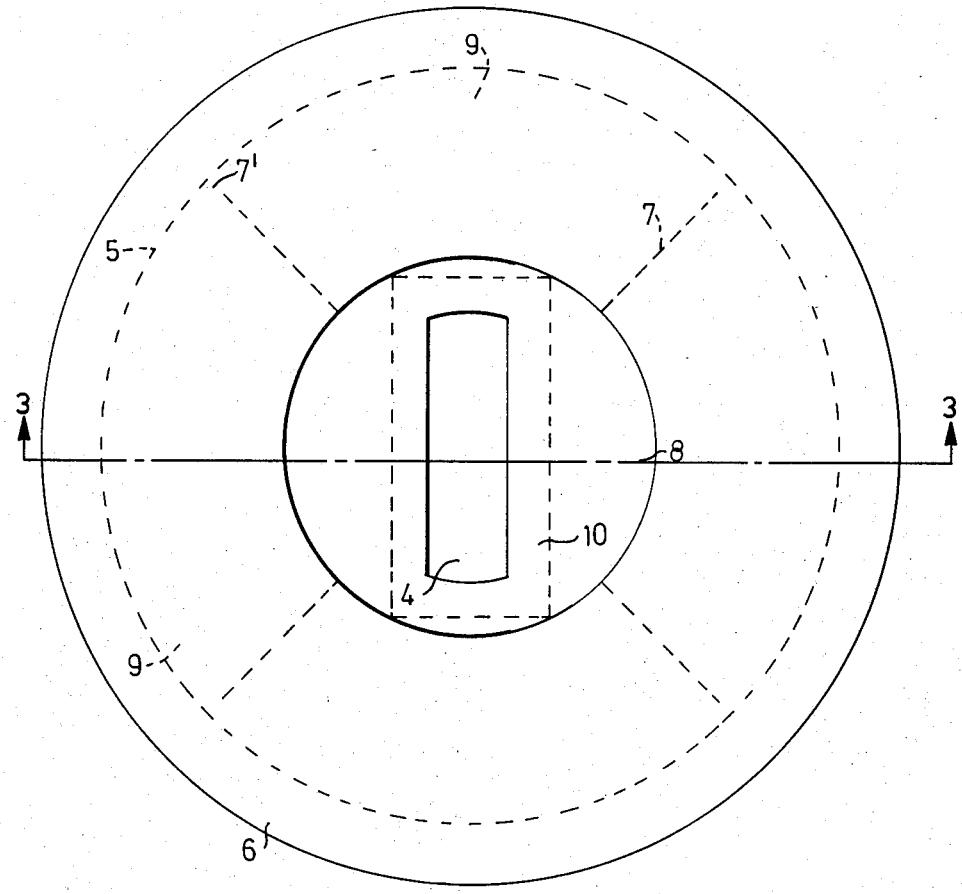
Figure 3:
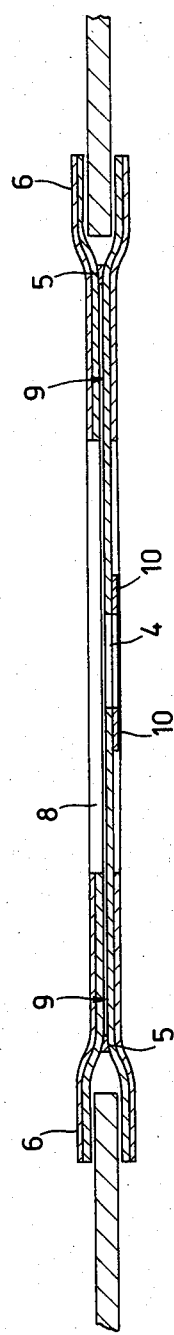

The invention will now be described in more detail with reference to an embodiment thereof illustrated in the accompanying drawings, in which FIG. 1 is a perspective view of an arrangement according to the invention in its in-use position, FIG. 2 is a plan view in larger scale of an embodiment of the disk forming part of the arrangement, and FIG. 3 is a cross section on line 3—3 of FIG. 2.

In the embodiment illustrated in FIG. 1, the surgical sheet comprises a first sheet-part 1 which is intended to cover the patient and the operating table, and a second sheet-part 2, which is intended to be placed over an anesthesis arch, to screen the anesthetizing personnel from the operating area. In the first sheet-part 1 there is formed a through-passing hole, which is preferably circular in shape and which when using the sheet is placed over the area of the patient in which the operation is to be performed. Permanently arranged in the hole is a disk 3 with a circular periphery. The disk is rotatable relative to the sheet and is provided with a central opening 4. The disk of the illustrated embodiment comprises a plurality of layers of liquid-impermeable and liquid-permeable absorbent material. The various layers are joined along a circular line 5, the circumference of which is smaller than, or essentially equal to the hole in the sheet. The disk 3 has a peripheral portion 6 located radially outwards of the circular line 5. This peripheral portion overlaps the sheet portions located nearest the hole, whereby the peripheral portions of one or more disk layers are located on the inside of the sheet and the peripheral portions of the remaining disk layers are located on the outside of the sheet. The surgical sheet itself suitably comprises two layers of non-woven material sandwiching therebetween a plastics film. The disk, which is described more fully hereinafter with reference to FIG. 2, is composed of similar material, and suitably comprises two laminates of a plastics film and a non-woven material. The material of which both the disk and the sheet are comprised is suitably chosen or treated so as to obtain but small friction between the mutually overlapping portions of the disk and the sheet.

When using an arrangement according to the invention, the surgical sheet is placed, while folded, with the disk located over the operation area, in the illustrated embodiment over the abdomen of the patient. The disk is turned so as to position the opening 4 along the intended surgical incision and is secured in its adjusted position to the patient, whereafter the sheet is unfolded. Because the disk can be rotated in accordance with the invention similar surgical sheets can be used for surgical operations on the breasts, abdomen and hip regions of patients. All that is required is for the sheet to be displaced laterally.

FIG. 2 illustrates the disk of the FIG. 1 arrangement in larger scale. As beforementioned, the disk 3 comprises two laminates, each comprising a plastics film and a non-woven material. The plastics films are lain against one another and the laminates are joined along the circular joining line 5 and along radial joining beads 7 extending from the circular line and inwards. The laminates are thus totally separated outside the circular line 5 with peripheral portions intended to lie on both sides of the peripheral portion of the hole in the surgical sheet.

Arranged in the laminate remote from the patient in the in-use position of the disk is a central area 8 having a diameter which is greater than the greatest extension of the opening 4. The area 8 provides a worksurface which is free from absorbent material on the underlying laminate. It is, of course, suitable to have around the actual incision an area which can be readily swabbed or dried. The area 8 and the joining lines 5,7 give rise to readily accessible pockets 9 between the two laminates. These pockets are suitable accomodations for various auxiliary devices to which rapid access is required during an operation. Absorbent material may also be placed in the pockets. This absorbent material can either be incorporated permanently during the manufacture of the sheet, or can be placed in the finished pockets manually. The disk 3 is adjusted to the desired position and is then secured in this position with the aid of a pressure-sensitive binder, which is placed in a region 10 around the opening 4.

The invention is not limited to the aforedescribed embodiment, and various modifications can be made within the scope of the following claims.

For example, the disk 3 need not be permanently fixed in the surgical sheet, but may have the form of a separate unit which is turned to the position desired and fixed in this position, either to the body of the patient or to the sheet.

It will be understood that the provision of pockets is not a necessity.

Prior to using the disk, the area 8 may be fully covered with a laminate structure which is formed similarly to the laminate layer in general but is separated therefrom by a perforated line.

I claim:

1. A surgical sheet having a relatively large circular hole therethrough adapted to be placed over an area of a patient where an operation is to be performed, a circular disk larger than said hole and having an elongated opening therethrough, the disk having at least two layers at least one of which comprises a liquid impermeable material, said layers being joined to each other about a circle of a diameter no greater than the diameter of said circular hole, the margins of said circular hole being received between said layers radially outwardly of said circle.

2. A surgical sheet as claimed in claim 1, and a self-adhesive binder about said elongated hole for securing the disk to the body of the patient.

3. A surgical sheet as claimed in claim 1, said layers being joined to each other radially inwardly of said circle only along radially extending lines, thereby to provide between said lines a plurality of pockets.

4. A surgical sheet as claimed in claim 1, the upper of said layers having a hole therethrough whose diameter is greater than the length of said elongated opening but less than that of said circle.

5. A surgical sheet as claimed in claim 4, said layers being secured together radially inwardly of said circle only along radially extending lines, thereby to provide a plurality of pockets between said lines.

6. A surgical sheet as claimed in claim 1, in which at least one of said layers is a laminate of said liquid impermeable material and a layer of absorbant non-woven material.

* * * * *